United States Patent
Kang

(10) Patent No.: US 11,051,640 B2
(45) Date of Patent: Jul. 6, 2021

(54) PILLOW

(71) Applicant: Suk-Jong Kang, Seoul (KR)

(72) Inventor: Suk-Jong Kang, Seoul (KR)

( * ) Notice: Subject to any disclaimer, the term of this patent is extended or adjusted under 35 U.S.C. 154(b) by 0 days.

(21) Appl. No.: 16/628,454

(22) PCT Filed: Jun. 11, 2018

(86) PCT No.: PCT/KR2018/006574
§ 371 (c)(1),
(2) Date: Jan. 3, 2020

(87) PCT Pub. No.: WO2019/009529
PCT Pub. Date: Jan. 10, 2019

(65) Prior Publication Data
US 2020/0205590 A1    Jul. 2, 2020

(30) Foreign Application Priority Data

Jul. 5, 2017  (KR) .......................... 10-2017-0085224

(51) Int. Cl.
*A47C 9/10* (2006.01)
*A47G 9/10* (2006.01)

(52) U.S. Cl.
CPC .................... *A47G 9/109* (2013.01)

(58) Field of Classification Search
CPC .. A47G 9/10; A47G 9/109; A47G 2009/1018; A47G 9/1081; A47C 21/00; A47C 20/00
See application file for complete search history.

(56) References Cited

U.S. PATENT DOCUMENTS 6,902,537 B1 *  6/2005  Geisert ................ A47G 9/1081
                                                              602/19
D529,325 S  *  10/2006  Maarbjerg ............... A47G 9/10
                                                              D6/601

FOREIGN PATENT DOCUMENTS

| JP | 2016-154573 A | 9/2016 |
| KR | 10-2010-0083685 A | 7/2010 |
| KR | 20-0476264 Y1 | 2/2015 |

(Continued)

OTHER PUBLICATIONS

International Search Report of corresponding PCT Application No. PCT/KR2018/006574—4 pages (dated Sep. 13, 2018).

(Continued)

*Primary Examiner* — Fredrick C Conley
(74) *Attorney, Agent, or Firm* — Knobbe Martens Olson & Bear LLP

(57) ABSTRACT

A pillow includes a body including a shoulder rest, a cervical spine rest and an occipital region rest; a first wing portion extending from the body to one side; and a second wing portion extending from the body to the other side. The occipital region rest includes a second inclined surface inclining downward at a predetermined angle toward a rear of the body and a recess portion recessed from an end of the second inclined surface toward an inside of the body to bring an upper occipital region into contact with a floor surface. According to the pillow, the respiratory tract is maximally opened when lying flat such that snoring is prevented and nose breathing is enabled, and since the load of the head is dispersed on the entire floor, the burden applied to the cervical vertebrae and shoulders by weight of the head itself can be reduced.

9 Claims, 6 Drawing Sheets

(56) References Cited

FOREIGN PATENT DOCUMENTS

KR 10-2015-0049415 A 5/2015
KR 10-2015-0091962 A 8/2015
KR 10-1559482 B1 10/2015

OTHER PUBLICATIONS

Office Action in corresponding KR Application No. 10-2017-0085224—4 pages (dated Aug. 29, 2017).

* cited by examiner

PILLOW

TECHNICAL FIELD

The present invention relates to a functional pillow that allows a user to get comfortable sleep.

BACKGROUND

In general, a pillow is filled with a cushion made of cotton or other chemical fibers in order to protect the head and give comfort to a user during sleep. This enables the user to get comfortable sleep.

According to a recent sleep medicine report, research results have been published that enough sleep improves growth development and learning ability. It is known that during sleep, the brain plays a role in obtaining and storing information through continuous activities.

Sleep is very important for children and adolescents who are growing up. However, children and adolescents have not been able to get enough sleep due to the stress caused by over-learning such as early education or the like. Due to the complexity of urban life, adults also undergo a lack of sleep, which weakens immunity and causes various diseases.

The cervical spine located in the neck area of the human body has a C-like shape toward the front side. If there is no pillow when a person gets sleep on the back, the cervical spine receives a downwardly-acting load. The neck and shoulder muscles become stiff in order to support the downwardly-acting load. Excessive stiffness of the muscles for a long time may lead to muscle pain. In order to alleviate such a problem, the role of a pillow that supports a person's head during sleep is important.

Recently, a pillow has been developed in consideration of the shape of the cervical spine. However, the pillow merely has a curved shape similar to the shape of the cervical spine.

SUMMARY

Embodiments of the present invention provide a functional pillow capable of comfortably supporting the user's head and shoulder when a user lies down on the back or on the side.

In accordance with an aspect of the present invention, there is provided a pillow including: a body including a shoulder rest, a cervical spine rest and an occipital region rest; a first wing portion extending from the body to one side; and a second wing portion extending from the body to the other side, wherein the occipital region rest includes a second inclined surface inclining downward at a predetermined angle toward a rear of the body and a recess portion recessed from an end of the second inclined surface toward an inside of the body to bring an upper occipital region into contact with a floor surface.

The shoulder rest may include a first inclined surface inclined at a predetermined angle toward the rear of the body.

The shoulder rest may include a pair of curved portions formed concavely at both sides of the first inclined surface toward the inside of the body.

The cervical spine rest may include a rounded protruding end which is convex upward of the body.

The second inclined surface may be formed obliquely with respect to the floor surface such that the height of the body gradually decreases toward the rear of the body.

The occipital region rest may include a seating recess recessed downward and inward of the body to surround a lower occipital region and a central occipital region.

The first wing portion and the second wing portion may be higher than a top horizontal plane of the body.

The first wing portion and the second wing portion may be lower than a top horizontal plane of the body.

As described above, according to the pillow of the present invention, the airway is opened to the maximum when a user lies down on the back. This enables the user to take nose breathing due to the snoring prevention effect and the reverse gravity effect. Since the weight of the head is distributed to the entire floor, is possible to reduce the burden on the cervical spine and the shoulder.

In addition, since the cervical spine and the backbone are located in a line in conformity with the user's body shape when the user lies down on the side, it is possible for the pillow to provide comfortable sleep to the user at any posture.

DETAILED DESCRIPTION

Figure 1:
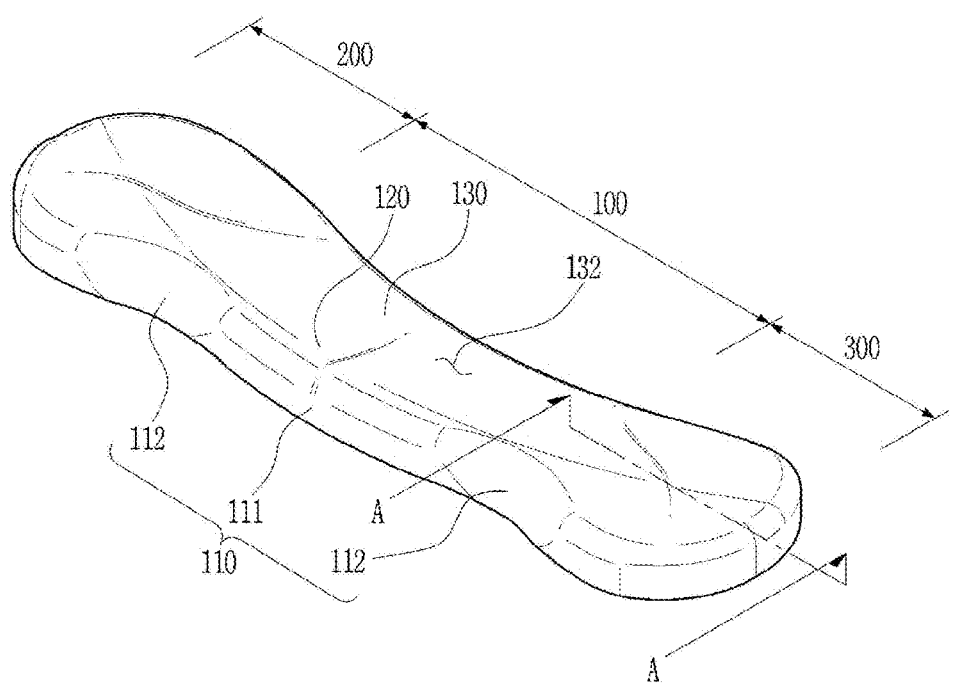
FIG. 1 is a perspective view showing a pillow according to an embodiment of the present invention.

Hereinafter, an embodiment of the present invention will be described in detail with reference to the accompanying drawings.

The terms or words used in the subject specification and the claims should not be construed as being limited to the common or dictionary meanings, but should be construed as meanings and concepts conforming to the technical idea of the present invention based on the principle that an inventor may properly define the concept of a term in order to best explain his or her own invention.

Therefore, the embodiments described in the subject specification and the configurations shown in the drawings are nothing more than most preferred example of the present invention, and do not represent all the technical ideas of the present invention. It goes without say that at the time of filing the subject application, there may be various equivalents and variations thereof.

Figure 2:
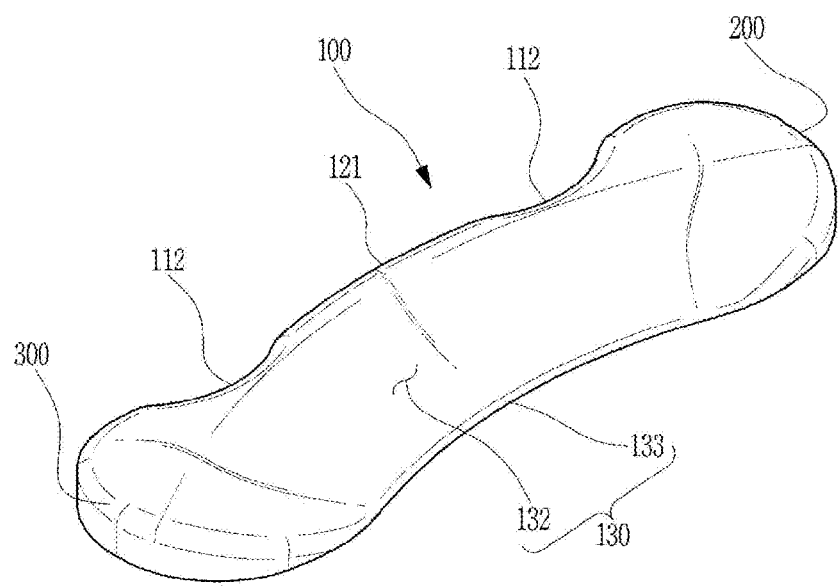
FIG. 2 is a perspective view showing the rear surface of the pillow shown in FIG. 1.
Figure 3:
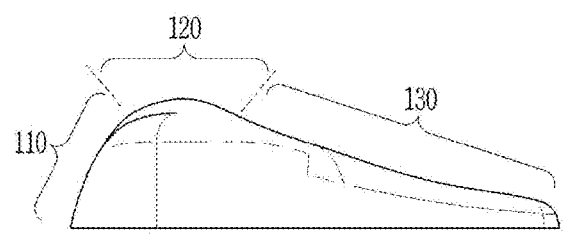
FIG. 3 is a side view of the pillow shown in FIG. 1.
Figure 4:
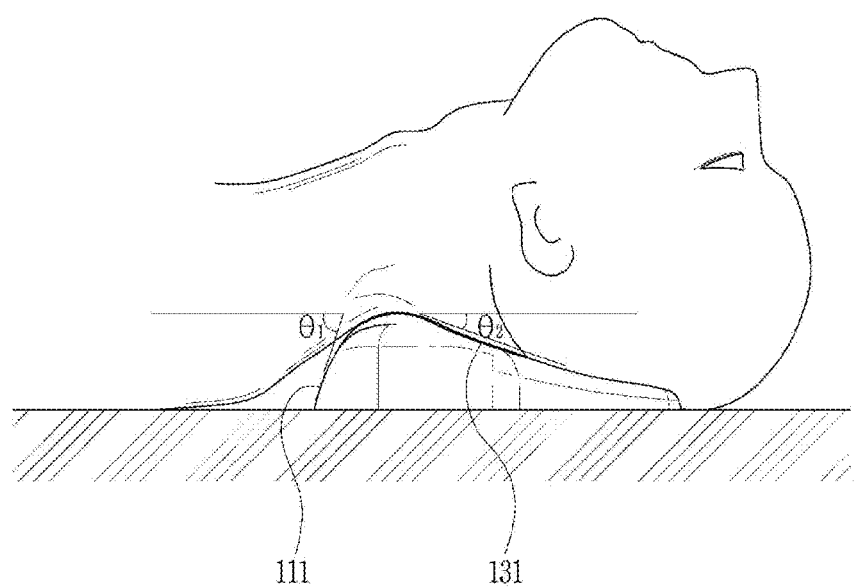
FIG. 4 is a view illustrating a state in which a user lies down on the back using the pillow shown in FIG. 3.
Figure 7:
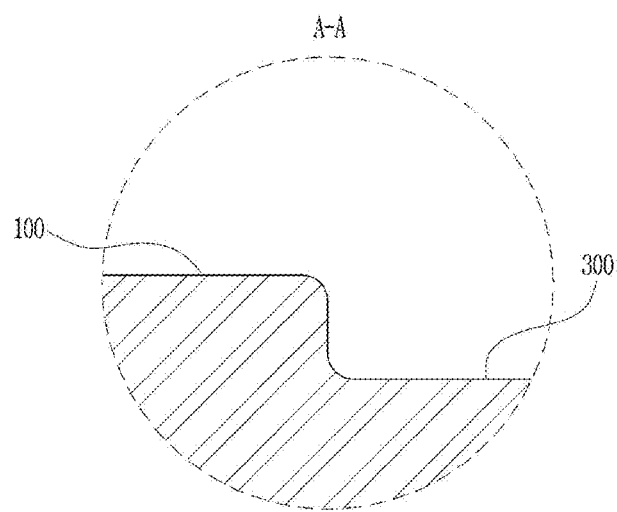
Figure 8:
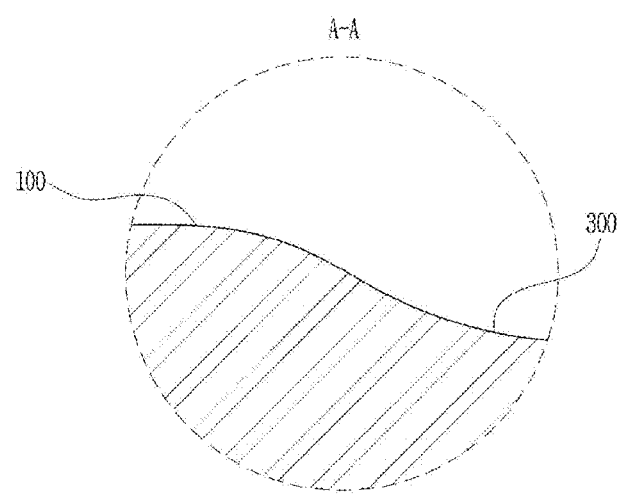
Figure 9:
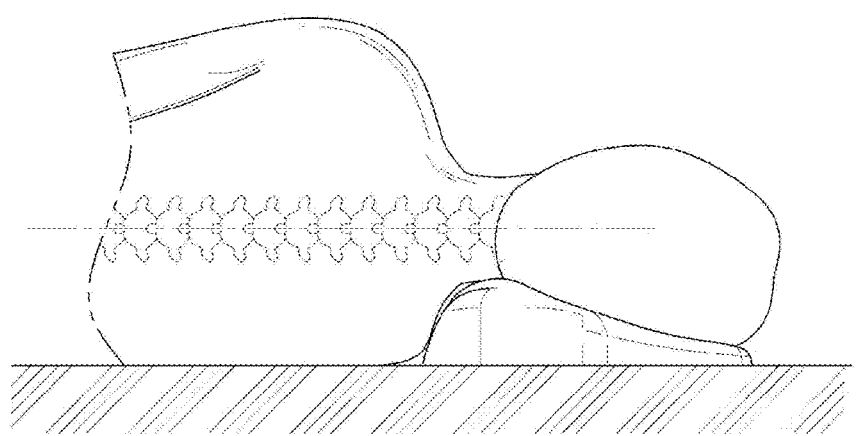
FIG. 9 is a view illustrating a state in which a user lies down on the side using the pillow shown in FIG. 3.

FIG. 1 is a perspective view showing a pillow according to an embodiment of the present invention. FIG. 2 is a perspective view showing the rear surface of the pillow shown in FIG. 1. FIG. 3 is a side view of the pillow shown in FIG. 1. FIG. 4 is a view illustrating a state in which a user lies down on the back using the pillow shown in FIG. 3. FIGS. 5 to 8 are views showing various forms of a wing portion taken along line A-A in FIG. 1. FIG. 9 is a view illustrating a state in which a user lies down on the side using the pillow shown in FIG. 3.

Referring to FIGS. 1 and 2, the pillow according to an embodiment of the present invention may include a body 100, a first wing portion 200 and a second wing portion 300.

The pillow of the present invention is preferably made of one of polyurethane, natural latex and memory foam, but is not limited thereto. Such a soft material provides a comfortable cushioning feeling to a user and has an excellent restoration force. Thus, deformation is very small even when the user flips during sleep.

As shown in FIG. 3, the body 100 may include a shoulder rest 110, a cervical spine rest 120 and an occipital region rest 130.

The shoulder rest 110 is provided on a front side of the body 100, and is formed vertically or obliquely with respect to a floor surface such that an upper part of the shoulder of the user is brought into close contact with the shoulder rest 110 when the user lies down on a back or on a side.

The shoulder rest 110 may include a first inclined surface 111 inclined at a predetermined first angle $\theta_1$ toward a rear of the body 100 as shown in FIG. 4. This is advantageous because when the user is lying down, an upper back surface of the user's shoulder is brought into close contact with the first inclined surface 111 of the shoulder rest 110, whereby the first inclined surface 111 can support the shoulder from below so that the head pressure applied to the shoulder is distributed. The first angle $\theta_1$ denotes an angle between the first inclined surface 111 and a plane parallel to the floor surface.

In addition, the shoulder rest 110 may include a pair of curved portions 112 concavely curved toward an inside of the body 100. The curved portions 112 are formed along a trajectory of an upper end of the shoulder to surround the upper end of the shoulder when the user lies down on the back or on the side. As a result, regardless of the posture taken by the user during sleep, the body 100 is brought closest to the user to enable the user to get sleep in a comfortable posture.

The cervical spine rest 120 supports the first to seventh cervical vertebrae arranged along a C-like curve of the cervical spine.

The cervical spine rest 120 may include a rounded protruding end 121 which is convex upward of the body 100. The protruding end 121 may achieve the same effect as tilting the cervical spine backward as much as possible to secure an airway during artificial respiration. That is, when the cervical spine is supported by the protruding end 121, the cervical spine is tilted backward as much as possible. Thus, the airway is opened as much as possible, and hence the breathing is made smooth. Nose breathing is induced because the mouth is naturally closed due to the snoring prevention effect and the reverse gravity effect. In addition, the face skin is relaxed by the reverse gravity effect, which makes it possible to prevent facial wrinkles and neck wrinkles.

The occipital region rest 130 supports a lower occipital region located above the first cervical vertebra and a central occipital region extending upward from the lower occipital region.

As shown in FIG. 4, the occipital region rest 130 may include a second inclined surface 131 inclined downward at a predetermined second angle $\theta_2$ toward the rear of the body 100. The second inclined surface 131 is formed obliquely with respect to the floor surface such that the height thereof gradually decreases toward the rear of the body 100. The second angle $\theta_2$ denotes an angle between the second inclined surface 131 and a plane parallel to the floor surface. The head is tilted back with respect to the cervical spine supported on the protruding end 121 by the second inclined surface 131, which makes it possible to obtain the aforementioned reverse gravity effect.

In addition, the occipital region rest 130 may include a seating recess 132 recessed downward and inward of the body 100 to surround the lower occipital region and the central occipital region. Since the occipital region of the user is brought into close contact with and stably wrapped by the seating recess 132, it is possible to induce comfortable sleep in a stable posture.

Meanwhile, the occipital region rest 130 may include a recess portion 133 formed at a rear end of the body 100 and recessed inward of the body 100 so as not to make contact with an upper occipital region. The recess portion 133 is formed in a concave semicircular shape at the rear end of the body 100. Thus, as shown in FIG. 4, when the user lies down on the back, the upper occipital region comes into contact with the floor surface. That is, by allowing the upper occipital region to make contact with a floor mattress or other flooring materials, it is possible to evenly distribute the head pressure on the floor and to reduce the head pressure applied to the cervical spine and the shoulder.

As described above, the shoulder rest 110 is brought into close contact with the user's shoulder so as to stably support the shoulder. The cervical spine is supported by the cervical spine rest 120 along the C-like curve from the first to seventh cervical vertebrae. The lower occipital region and the central occipital region are seated on the occipital region rest 130. Thus, the head pressure and the body pressure are properly separated, and the head pressure applied to the cervical spine and the shoulder is effectively dispersed.

Meanwhile, the first wing portion 200 is provided on one side of the body 100 and is formed to extend outward with respect to the body 100. The second wing portion 300 is provided on the other side of the body 100 and is formed to extend outward with respect to the body 100. At this time, the first wing portion 200 and the second wing portion 300 may be higher than or lower than a top horizontal plane of the body 100.

The first wing portion 200 and the second wing portion 300 may be stepped at a right angle with respect to the body 100, or may obliquely extend from the body 100 so that the height thereof gradually increases or decreases. This is because the height, shoulder height, shoulder width, and cervical spine height vary from person to person.

Figure 5:
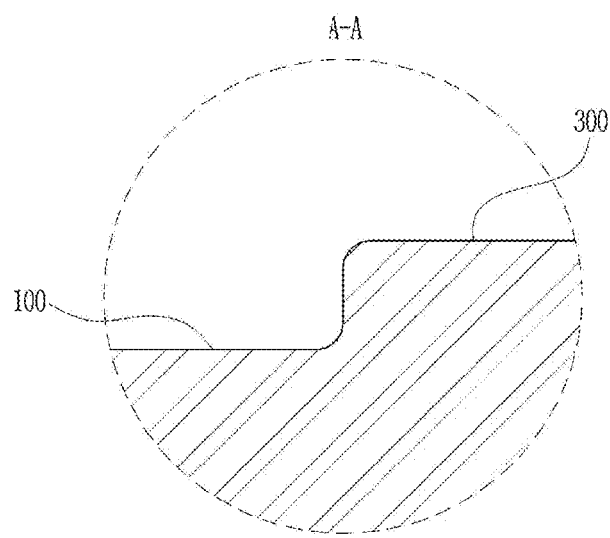
FIGS. 5 to 8 are views showing various forms of a wing portion taken along line A-A in FIG. 1.
Figure 6:
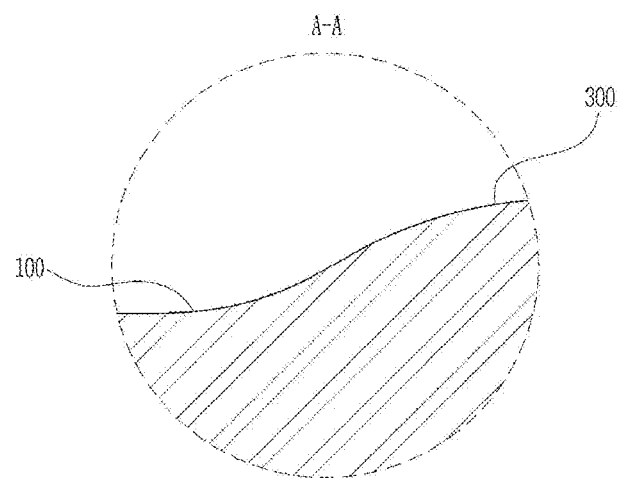

When a user having a large shoulder width lies down on the side, the backbone and the cervical spine are not arranged in a line due to the height of the shoulder, which poses a problem that the cervical spine is bent downward. In order to solve this problem, as shown in FIGS. 5 and 6, the first wing portion 200 and the second wing portion 300 are formed higher than the body 100 to support the head of the user so that the backbone and the cervical spine are arranged in a line. At this time, the backbone and the cervical spine of the user are arranged in a line, but the head of the user is naturally inclined slightly downward along the second inclined surface 131 of the occipital region rest 130.

On the contrary, when a user having a small shoulder width lies down on the side, the backbone and the cervical spine are not arranged in a line due to the height of the shoulder, which poses a problem that the cervical spine is bent upward. In order to solve this problem, as shown in FIGS. 7 and 8, the first wing portion 200 and the second wing portion 300 are formed to be lower than the body 100 to support the head of the user so that the backbone and the cervical spine are arranged in a line. At this time, the backbone and the cervical spine of the user are arranged in a line as shown in FIG. 9, but the head of the user is naturally inclined slightly downward along the second inclined surface 131 of the occipital region rest 130.

As described above, according to the pillow of the present invention, the airway is opened to the maximum when a user lies down on the back. This enables the user to take nose breathing due to the snoring prevention effect and the reverse gravity effect. Since the weight of the head is distributed to the entire floor, it is possible to reduce the burden on the cervical spine and the shoulder.

In addition, since the cervical spine and the backbone are located in a line in conformity with the user's body shape when the user lies down on the side, it is possible for the pillow to provide comfortable sleep to the user at any posture.

While the present invention has been described above by way of the limited embodiments and drawings, the present invention is not limited thereto. It goes without saying that those skilled in the art to which the invention pertains may make various modifications and variations without departing from the technical spirit of the present invention and the equivalents of the claims to be recited below.

EXPLANATION OF REFERENCE NUMERALS

100: body
110: shoulder rest
111: first inclined surface
112: curved portion
120: cervical spine rest
121: protruding end
130: occipital region rest
131: second inclined surface
132: seating recess
133: recess portion
200: first wing portion
300: second wing portion

What is claimed is:

1. A pillow configured to be laid on a substantially flat surface for a use in resting a shoulder and an occipital region of a head of a user, the pillow comprising:
    a body including, when the user lies on one's back, a shoulder rest configured to make a contact with an upper side of the shoulder, a cervical spine rest configured to support a cervical spine of the user and an occipital region rest configured to rest on a lower part and a central part of the occipital region;
    a first wing portion extending in a first direction from the body; and
    a second wing portion extending in a second direction from the body, the second direction being opposite to the first direction,
    wherein the occipital region rest includes a first inclining part whose thickness becomes thinner as it goes to an upper side of the head, the first inclining part having an inclining surface inclining at a first predetermined angle from a surface parallel to the substantially flat surface toward the substantially flat surface, the occipital region rest further including a recess portion formed at a rear end of the body and recessed from an end of the first inclining part toward an inside of the body to so that an upper occipital region of the user does not make contact with the recess portion and the upper occipital region makes a contact with the substantially flat surface.

2. The pillow of claim 1, wherein the shoulder rest includes a second inclining part having an inclining surface inclined at a second predetermined angle from the surface parallel to the substantially flat surface toward the substantially flat surface.

3. The pillow of claim 2, wherein the shoulder rest includes a pair of curved portions formed concavely at both of lateral sides of the second inclining part.

4. The pillow of claim 1, wherein the cervical spine rest includes a rounded protruding end which is convex upward of the body.

5. The pillow of claim 1, wherein the inclining surface of the first inclining part is formed obliquely with respect to the substantially flat surface such that the height of the body gradually decreases toward a rear of the body.

6. The pillow of claim 1, wherein the occipital region rest includes a seating recess recessed downward and inward of the body to surround a lower occipital region and a central occipital region in a back surface of the user's occipital.

7. The pillow of claim 1, wherein the first wing portion and the second wing portion are higher than a top horizontal plane of the body.

8. The pillow of claim 1, wherein the first wing portion and the second wing portion are lower than a top horizontal plane of the body.

9. The pillow of claim 1, wherein the shoulder rest comprises a pair of curved recess portions formed at a front end of the body and recessed toward the body while the recess portion of the occipital region rest is formed at the rear end of the body.

* * * * *

UNITED STATES PATENT AND TRADEMARK OFFICE
CERTIFICATE OF CORRECTION

PATENT NO. : 11,051,640 B2
APPLICATION NO. : 16/628454
DATED : July 6, 2021
INVENTOR(S) : Suk-Jong Kang Page 1 of 1

It is certified that error appears in the above-identified patent and that said Letters Patent is hereby corrected as shown below:

In the Specification

In Column 2 at Line 13 (approx.), after "floor," insert --it--.

In the Claims

In Column 6 at Line 12 (approx.), Claim 1, delete "the body to" and insert --the body--.

Signed and Sealed this
Tenth Day of May, 2022

Katherine Kelly Vidal
*Director of the United States Patent and Trademark Office*